US009682010B2

(12) United States Patent
Hoke et al.

(10) Patent No.: US 9,682,010 B2
(45) Date of Patent: Jun. 20, 2017

(54) SYSTEMS AND METHODS FOR NASAL IRRIGATION (75) Inventors: Martin R. Hoke, Lakewood, OH (US); Paul R. Metcalfe, Solon, OH (US)

(73) Assignee: RhinoSystems, Inc., Lakewood, OH (US)

(*) Notice: Subject to any disclaimer, the term of this patent is extended or adjusted under 35 U.S.C. 154(b) by 1203 days.

(21) Appl. No.: 13/276,456

(22) Filed: Oct. 19, 2011

(65) Prior Publication Data

US 2012/0078166 A1 Mar. 29, 2012

Related U.S. Application Data (62) Division of application No. 12/042,906, filed on Mar. 5, 2008, now Pat. No. 8,048,023.

(Continued)

(51) Int. Cl.
*A61H 1/00* (2006.01)
*A61H 35/04* (2006.01)

(Continued)

(52) U.S. Cl.
CPC ........... *A61H 35/04* (2013.01); *A61M 1/0064* (2013.01); *A61M 3/0283* (2013.01);

(Continued)

(58) Field of Classification Search
CPC ........ A61M 2210/0618; A61M 3/0262; A61M 3/0241; A61M 3/0258; A61M 3/0283;

(Continued)

(56) References Cited

U.S. PATENT DOCUMENTS 1,248,891 A 12/1917 Nichols
1,487,252 A 3/1924 Loré

(Continued)

FOREIGN PATENT DOCUMENTS

DE 472 626 C 3/1929

OTHER PUBLICATIONS

International Search Report for International Application No. PCT/US08/56003, mailed Jun. 24, 2008.

(Continued)

*Primary Examiner* — Kevin C Sirmons
*Assistant Examiner* — William Carpenter
(74) *Attorney, Agent, or Firm* — Fay Sharpe LLP (57) ABSTRACT Systems and methods for nasal irrigation are provided in which a nasal irrigation device includes a source of saline, an effluent receptacle, a nasal interface, a vacuum source, a fluid passageway to communicate the source of saline with the effluent receptacle through the nasal interface and a nasal cavity of the user, and a switch and valve assembly for selectively controlling the vacuum source and flow of the saline through the fluid passageway. The saline source is disposed relative to the device to provide gravitational inducement of saline to the nasal interface in engagement to the device user's nostrils. A combination of the gravitational inducement and the relative vacuum from the effluent receptacle generates a fluid flow for irrigating, cleansing and massaging the nasal cavity and ostia of the user. The entire device is assembled as a hand-held device for convenient lifting and disposal against the user's nostrils.

12 Claims, 7 Drawing Sheets

Related U.S. Application Data (60) Provisional application No. 60/895,180, filed on Mar. 16, 2007, provisional application No. 60/893,191, filed on Mar. 6, 2007.

(51) Int. Cl.
*A61M 3/02* (2006.01)
*A61M 1/00* (2006.01)
*A61H 33/04* (2006.01)

(52) U.S. Cl.
CPC ..... *A61M 3/0287* (2013.01); *A61H 2033/048* (2013.01); *A61H 2201/105* (2013.01); *A61M 1/0039* (2013.01); *A61M 3/0241* (2013.01); *A61M 2210/0618* (2013.01)

(58) Field of Classification Search
CPC .. A61M 15/00; A61M 1/0023; A61M 1/0064; A61M 3/02; A61M 1/0039; A61M 1/0031; A61M 1/0021; A61M 1/0019
USPC ........ 604/27, 28, 30, 35, 36, 39, 41, 43, 45, 604/500, 514, 73, 80, 94.01, 131, 140, 604/151, 173, 181, 257, 261, 264, 275, 604/276, 278
See application file for complete search history.

(56) References Cited

U.S. PATENT DOCUMENTS

| | | | |
|---|---|---|---|
| 1,502,163 A | 7/1924 | Sprague | |
| 1,603,758 A | 10/1926 | Fisher | |
| 1,856,811 A * | 5/1932 | Inaki | A61M 3/0262 604/183 |
| 2,078,180 A * | 4/1937 | Kronenberg | 604/28 |
| 2,280,992 A | 4/1942 | Wright et al. | |
| 2,511,973 A | 6/1950 | De La Sierra, Jr. | |
| 3,847,145 A * | 11/1974 | Grossan | A61H 35/04 601/160 |
| 4,029,095 A | 6/1977 | Pena | |
| 4,403,611 A | 9/1983 | Babbitt et al. | |
| 4,637,814 A | 1/1987 | Leiboff | |
| 4,655,197 A | 4/1987 | Atkinson | |
| 5,788,683 A | 8/1998 | Martin | |
| 5,899,878 A | 5/1999 | Glassman | |
| 5,928,190 A | 7/1999 | Davis | |
| 6,099,494 A | 8/2000 | Henniges et al. | |
| 6,238,377 B1 * | 5/2001 | Liu | A61H 35/04 604/289 |
| 6,241,705 B1 * | 6/2001 | Ko-Wen | A61M 3/0241 604/73 |
| 6,361,521 B1 * | 3/2002 | Erickson | A61M 3/0262 128/200.22 |
| 6,520,384 B2 | 2/2003 | Mehta | |
| 6,540,718 B1 | 4/2003 | Wennek | |
| 6,561,188 B1 | 5/2003 | Ellis | |
| 6,669,059 B2 | 12/2003 | Mehta | |
| 6,688,497 B2 | 2/2004 | Mehta | |
| 6,715,485 B1 * | 4/2004 | Djupesland | 128/203.15 |
| 6,736,792 B1 | 5/2004 | Liu | |
| 6,907,879 B2 * | 6/2005 | Drinan et al. | 128/202.22 |
| 7,029,705 B2 | 4/2006 | Fuhr | |
| 2002/0099331 A1* | 7/2002 | Burchfield | A61M 3/0241 604/94.01 |
| 2002/0151836 A1 | 10/2002 | Burden | |
| 2005/0028812 A1 | 2/2005 | Djupesland | |
| 2008/0119782 A1 | 5/2008 | Steinman et al. | |
| 2008/0154183 A1 | 6/2008 | Baker et al. | |
| 2008/0183128 A1 | 7/2008 | Morriss et al. | |
| 2008/0208112 A1 | 8/2008 | Bensoussan | |

OTHER PUBLICATIONS

Extended European Search Report for International Application No. PCT/US08/56003, mailed Aug. 20, 2012.
Partial European Search Report dated May 28, 2015 for EP 14171515.1.

* cited by examiner

SYSTEMS AND METHODS FOR NASAL IRRIGATION

This application claims the priority, as a divisional, of U.S. application Ser. No. 12/042,906, filed Mar. 5, 2008 now U.S. Pat. No. 8,048,023; which claimed the benefit of U.S. provisional application No. 60/895,180, filed Mar. 16, 2007 and U.S. provisional application No. 60/893,191, filed Mar. 6, 2007, the disclosures of which are incorporated herein by reference.

TECHNICAL FIELD

The presently disclosed embodiments generally relate to methods and devices for irrigating and rinsing the nasal cavity and anatomical openings thereto.

BACKGROUND

Nasal and sinus disease and sinus related syndromes and symptoms are a common clinical problem with considerable patient morbidity, substantial direct costs, and a significant, negative impact on the quality of life for those who are afflicted. The four primary categories of afflicted groups are: 1) individuals with acute and chronic rhinosinusitis; 2) individuals with acute upper respiratory infections, 3) individuals who suffer from allergic rhinitis; and 4) individuals with chronic snoring problems. These four categories amount to millions of people who suffer from nasal congestion on a daily basis.

The Centers for Disease Control and Prevention estimated the number of cases of chronic rhinosinusitis in the United States to be 35 million in 1994, a prevalence of about 13.5%, or about 40.5 million Americans adjusted for 2007 population figures (estimates from the National Health Interview Survey, 1994. *Vital Health Stat* 10. 1995:261-520.) Rhinosinusitis was the fifth most common diagnosis for which antibiotics were prescribed from 1985 to 1992 (McCaig L F, Hughes J M. Trends in antimicrobial drug prescribing among office-based physicians in the United States. *JAMA*. 1995; 273:214-219). In 1996 rhinitis accounted for approximately 26.7 million office and emergency department visits resulting in $5.8 billion in direct costs (Ray N F, Baraniuk J N, Thamer M, et al. Healthcare expenditures for sinusitis in 1996: contributions of asthma, rhinitis, and other airway disorders. *J Allergy Clin Immunol*. 1999; 103:408-414).

Allergic rhinitis has been reported to affect approximately 17% of the general population in the United States (Ray N F, Baraniuk J N, Thamer M, et al. Healthcare expenditures for sinusitis in 1996: contributions of asthma, rhinitis, and other airway disorders. *J Allergy Clin Immunol*. 1999; 103:408-414), and in selected pediatric populations might be present in up to 42% (Wright A L, Holberg C J, Martinez F D, Halonen M, Morgan W, Taussig L M. Epidemiology of physician-diagnosed allergic rhinitis in childhood. Pediatrics 1994; 94:895-901). This amounts to an upper estimate of 60 million Americans.

According to the National Sleep Foundation, snoring currently affects approximately 90 million American adults, 37 million on a regular basis.

The combined number of those who suffer from rhinosinusitis, allergic rhinitis, and snoring amounts to a high estimate of 190 million Americans and a low estimate of 128 million Americans, not accounting for double-counting individuals who may be in two or more categories. Adopting the conservative assumption of over 40% duplication yields an estimate of 75 million Americans who suffer from adverse sinus symptoms and would benefit from an effective therapy to relieve those symptoms.

Bathing the nasal and sinus cavities with lightly-salted water to wash away encrusted mucous, irritants, and foreign particles for the purpose of improving airflow and relieving nasal congestion has been widely practiced across many cultures for literally thousands of years. More recently, and particularly since about 1990, a significant number of peer-reviewed clinical trials have been undertaken at leading American and European medical schools and research centers testing whether the anecdotal claims of relief from the symptoms of nasal maladies as a result of nasal irrigation, are well founded and pass scientific scrutiny. (Harvey R, Hannan S A, Badia L, Scadding G. Nasal saline irrigations for the symptoms of chronic rhinosinusitis. *Cochrane Database of Systematic Reviews* 2007, Issue 3. Art No.: CD006394. DOI: 10.1002/14651858.CD006394.pub2.)

Several clinical studies demonstrate that regular use of nasal irrigation is an effective therapy to relieve the symptoms of chronic and acute rhinosinusitis, including statistically significant findings of reduced nasal congestion, increased nasal passage airflow, reduced doctor visits, reduced number of prescriptions for sinus medicine, and improved quality of life. (Rabago D, Zgierska A, Mundt M, et al. Efficacy of daily hypertonic saline nasal irrigation among patients with sinusitis: A randomized controlled trial. *Journal of Family Practice*. 2002; 51(12):1049-1055.) Other clinical studies indicate that regular nasal irrigation is a beneficial therapy for the treatment of allergy-related nasal symptoms. (Garavello W, Romagnoli M, Sordo L, et al. Hypersaline nasal irrigation in children with symptomatic seasonal allergic rhinitis: a randomized study. *Pediatric allergy and immunology*. 2003; 14:140-143.) Other as yet unpublished clinical studies are currently underway, testing whether nasal irrigation is an effective preventive therapy with respect to the common cold and snoring.

These studies indicate that nasal irrigation is a clinically proven method for treating the symptoms of sinus-related disease by exposing the nasal cavity to a streaming volume of saline. While the exact mechanism by which nasal irrigation's effectiveness is achieved is not yet well understood by the medical and scientific research community, it is likely multifaceted and includes a number of physiological effects which individually or in concert may result in an improved ability of the nasal mucosa to reduce the pathologic effects of inflammatory mediators and other triggers of allergic rhinitis, asthma and other chronic mucosal reactions, as follows. First, it rinses the entire interior of the nasal cavity, washing away encrustations that may be blocking the multiple ostia that connect the sinus cavities to the nasal cavity, thereby allowing the sinus cavities to properly drain into the nasal cavity and making the sinus cavities a much less attractive breeding ground for the colonization of bacteria. Second, it decreases the viscosity of the mucous in the nasal cavity, thereby greatly reducing the formation of interior encrustations. Third, it leaves a small residue of saline on the interior surfaces of the nasal cavity, including the openings to the sinus cavities and sometimes in the sinus cavities themselves. This is beneficial because saline has an inherently antiseptic quality that hinders the growth of bacteria. Fourth, exposure of the turbinates, vascular tissue that warms and humidifies the air inspired through the nose before it reaches the lungs, to saline causes them to reduce in size, thereby reducing nasal congestion. Fifth, it improves mucociliary clearance as a result of increased ciliary beat frequency, which improves the ability of the mucosa to perform its natural, flushing function. Sixth, the saline may wash away airborne bacteria, viral particles, irritants and other foreign particles that cause infections and allergies. (See: Ponikau J U, Sherris D A, Kephart D M, et al. Striking deposition of toxic eosinophilic major basic protein in mucus: Implications for chronic rhinosinusitis. *J Allergy Clin Immunol.* 2005; 116(2):362-369; Ozsoylu S. Nose drops and the common cold. *Eur J Pediatr.* 1985; 144:294; Karadag A. Nasal saline for acute sinusitis. *Pediatrics.* 2002; 109:165; Kurtaran H, Karadag A, Catal F, et al. A reappraisal of nasal saline solution use in chronic sinusitis. *Chest.* 2003; 124:2036-2037; Georgitis J W. Nasal hyperthermia and simple irrigation for perennial rhinitis. Changes in inflammatory mediators. *Chest.* 1994; 106:1487-1492; Talbot A R, Herr T M, Parsons D S. Mucocilliary clearance and buffered hypertonic saline solution. *Laryngoscope.* 1997; 107:500-503; Boek W M, Graamans K, Natzijl H, et al. Nasal mucociliary transport: New evidence for a key role of ciliary beat frequency. *Laryngoscope.* 2002; 112:570-573.)

There are three methods by which the nasal cavity can be irrigated: gravity, pressure, and suction.

Gravity-based devices allow the flow of saline into the nasal cavity by, for example, inserting the tip of a teapot-like spout into one nostril and pouring the saline into it. The saline then flows around the posterior margin of the nasal septum and out the other nostril of the user. An example of a gravity-based device is the neti pot. However, the awkward physical position required to accomplish such a rinse is difficult for many people, and the free flowing effluent from the nasal passageway is messy so that substantial clean up procedures are necessary.

Pressure-based devices pump the saline into the nasal cavity, again, by introducing the saline into one nostril, forcing it under pressure around the posterior margin of the nasal septum, and allowing it to drain out the other nostril. This can be done, for example, by placing the nozzle of a saline-filled, flexible plastic tube or bottle into one nostril and squeezing it, thereby injecting the saline into one nostril, through the nasal cavity, and out the other nostril. Although this avoids some of the physical awkwardness needed to achieve a gravity forced flow, the problems of messiness and the attendant inconvenience of cleaning remain. In addition, the varied pressures imparted by a squeeze tube can impart undesired, painful, and even harmful pressures throughout the nasal passageway, and particularly on the Eustachian tube ostia. Thus, this requires some acquired skill for proper use.

Prior devices have generally not utilized suction. The most common method by which suction is used to perform nasal irrigation is as simple as the user cupping a small amount of lightly salted water in his palm and sniffing it into his nostrils.

There is presently no practical device that offers a user the ability to practice nasal irrigation using all three delivery methods in a single device.

There is presently no practical device that offers a user the ability to practice nasal irrigation in a combination of either gravity and pressure, gravity and suction, or pressure and suction in a single device, nor is there a device that offers a powered mechanism in any of the three foregoing combinations.

There is presently no practical device that offers a user the ability to practice nasal irrigation using suction alone.

There is a need for a convenient hand-held device that can safely irrigate the nasal cavity with a controlled, gentle supply, draw the irrigant through the nasal cavity under the influence of gentle powered suction, collect the effluent safely in a manner facilitating quick and easy disposal, and is readily adaptable to a wide variety of nasal dimensions.

SUMMARY

A nasal irrigation device is provided for therapeutic irrigating of a nasal cavity of a user. The device includes a source of saline solution, an effluent receptacle, a nasal interface, a vacuum source, fluid passageways and a switch and valve assembly. The nasal interface engages a device user's nostrils to deliver saline solution by gravity from the source to the nasal cavity. The source of saline solution communicates with the effluent receptacle through the fluid passageway, the nasal interface, and the device user's nasal cavity. The switch and valve assembly controls the vacuum source and flow of saline solution through the fluid passageway. It is understood that in addition to the aforementioned saline solution, alternative irrigants may also be incorporated into use with the device.

In accordance with another aspect of the present embodiments, a pressure source forms a relative pressure in the source of saline solution to supplement or replace gravitational inducement of the solution towards the interface.

In yet another embodiment, the nasal irrigation device comprises a hand-held assembly including the saline solution source, the effluent receptacle, the nasal interface, the vacuum source, the fluid passageway and the switch. A power source such as a battery pack controls the supply of energy to an electric motor and pump assembly functioning as the vacuum source.

Yet another embodiment comprises a hand-held nasal irrigation device including the source of saline solution, the effluent receptacle, the nasal interface, the fluid passageway and a valve for selectively controlling the flow of the saline solution through the fluid passageway wherein the effluent receptacle is disposed relative to the source and the nasal interface for gravitational inducement of the saline solution through the device. Neither a vacuum source nor a pressure source is included in this embodiment, as gravity is the sole source of inducement of the saline solution through the device and the nasal cavity.

A method for irrigating a nasal cavity is also provided including sealing the nares of a user to a hand-held device including an associated fluid passageway in communication with a saline solution source and a saline effluent receptacle. The passageway, source and receptacle are integrally assembled in the hand-held device. A relative vacuum is applied to the effluent receptacle with a powered suction source also included in the hand-held device. The saline solution is released from the source into the passageway and the nasal cavity whereby a flow of the saline through the nares and around a posterior margin of a nasal septum of the user irrigates the nasal cavity.

BRIEF DESCRIPTION

Figure 3:
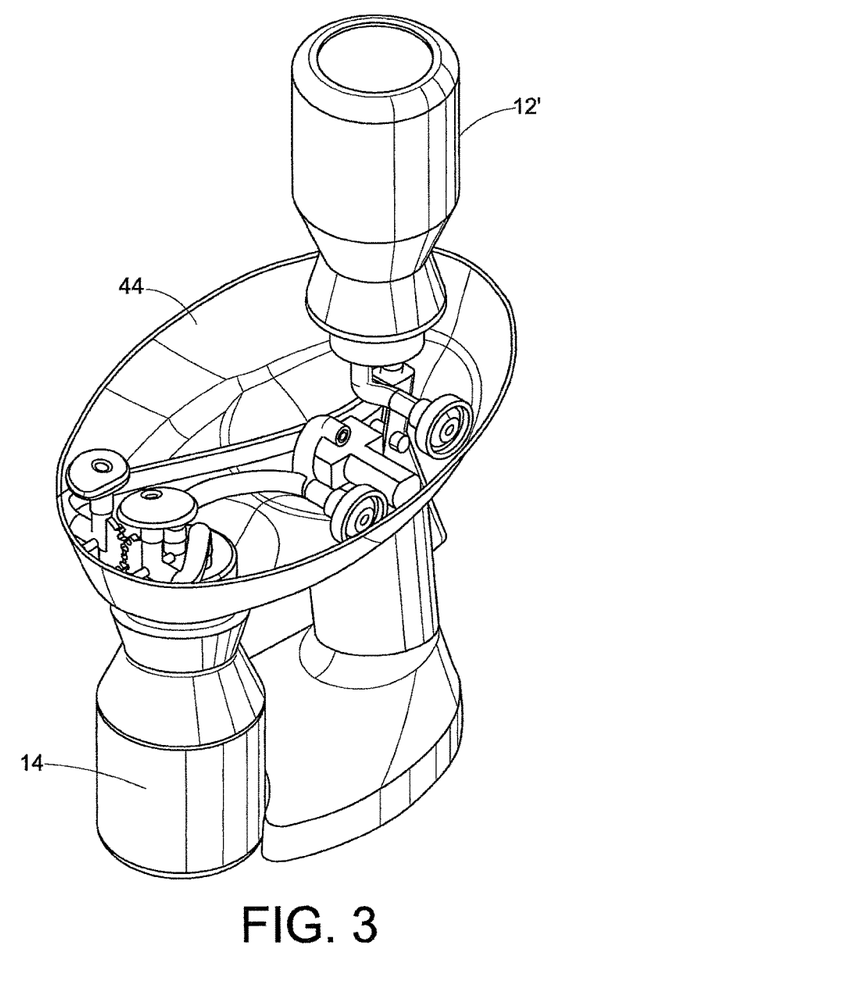
FIG. 3 is a sectional perspective view showing a top wall removed for a clearer viewing of the housed elements of the assembly of the embodiment of FIG. 1.

The Figures show a nasal irrigation device or tool, preferably easily hand-held in use, which provides a more convenient, cleaner, more pleasant, and more effective irrigating therapy for the nasal cavity and sinus ostia. The device 10 is principally comprised of three components, an irrigant source bottle 12, containing, for example, saline solution, a receptacle bottle 14 for receiving saline effluent, and a controller 16 for controlling the communication of fluid from the first bottle, through the nasal cavity and into the second bottle as will be hereinafter more fully explained. The bottles 12,14 may be of any of a variety of shapes and may be attached to the controller in any variety of manners, such as with a threaded neck, a pinch fit, a bayonet mount, or the like. A typical size will accommodate 6 to 10 ounces of fluid. It is envisioned that the first bottle 12, upon being emptied as the result of having been used, can subsequently be used as the second bottle 14 which upon being filled with effluent by use can then be thrown away. Accordingly, the provision of a single bottle provides both the first bottle of saline source at one time, and then the effluent receptacle 14 at a next time. It is also within the intended scope of the present embodiments that the bottles may be refillable, or reusable, or may even be permanent chambers within the controller 16 that may be filled or emptied upon completion of an irrigating therapy. In FIG. 3, bottle 12' lacks a top wall such that it is open ended for refilling. Although saline solution is mentioned here as the exemplary irrigant, the embodiments are intended to include alternate irrigants of a variety of saline mixes including flavorants or medicines.

The controller 16 includes a handle portion 20 and a housing 22. The handle 20 is intended to function as a pistol-type grip including a trigger 24 and a pedestal base 26 having a flat bottom wall 28 to allow the entire assembly 10 to stand upright on a flat surface such as a bathroom vanity or kitchen countertop when not in use. The base 26 also includes an arcuate cutout 30 shaped to match a contour of the effluent bottle 14 in a manner to facilitate support and positioning of the bottle 14 relative to the controller 16. The handle assembly 20 is configured to accommodate either a right-handed or left-handed grip as the trigger 24 and the ergonomic configuration of the handle are intended to be handed-neutral. The housing 22 includes a top cover 34 including a source bottle opening 36 through which the saline source bottle extends and a nasal interface 38 disposed to engage the nares (nostrils) 32 of a user's nose with a good seal for forming an integral fluid passageway between the source bottle 12 and the effluent bottle 14 through a user's nasal cavity. The nasal interface is comprised of first and second nozzles 40, 42, which are also called nasal cushions, and which can swivel or pivot as may be necessary to form a cushioned seal against the nares, depending upon the personal anatomy of the user. A positive seal between the nasal cushions and a user's nares is essential to the successful operation of the device with respect to both its therapeutic function as well as to its distinguishing qualities of convenience, cleanliness and neatness. Therefore, the cushions 40, 42 are especially configured to facilitate such a seal. In operation, leakage from the nasal cavity is precluded so long as the engaging seal between the interface 38 and nostrils is maintained. It can be seen that the nasal cushions have a truncated elliptical configuration in a plane view and with a somewhat flattened conical configuration in cross section. The cushion opening is slightly spaced from the middle of the cushion to provide a more extended sealing surface for engaging the outer edges of the nares than the inner edges that are bordered by the nose columella. The cushions 40, 42 may alternatively comprise communal nozzles that are easily removable and replaceable for convenient washing or for the attachment of a personal set of nozzles corresponding to distinct individual users. Adjustment to accommodate different nose sizes is accomplished by rotating supporting swivel gears 56 or by other generally understood mechanical means.

The overall configuration of a nasal interface is intended to achieve a positive, fluid-tight seal upon gentle but firm urging of the nozzles 40, 42 against the nares 32 of a user.

Figure 6:
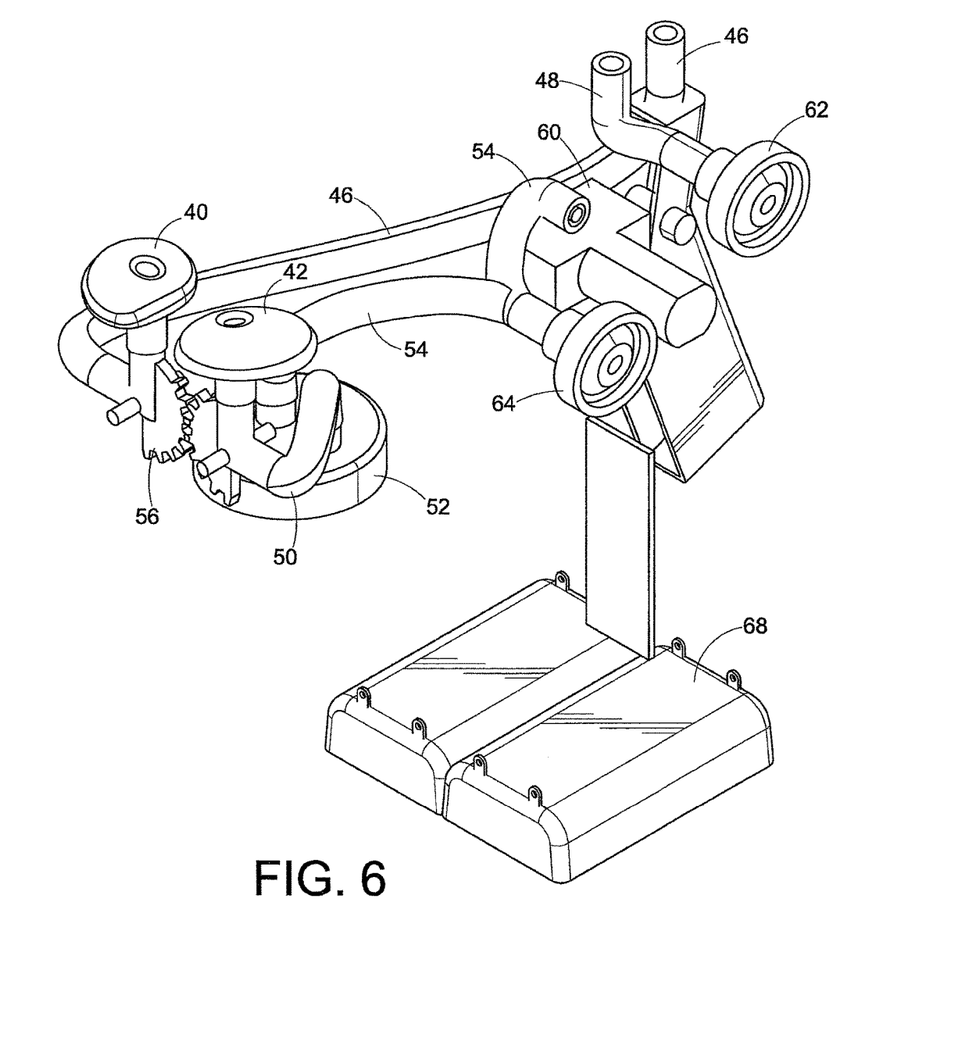
FIG. 6 is a partial view of the device internal components wherein all outer walls have been removed; and, FIG. 7 is a perspective view of another alternative embodiment wherein a handle is disposed below a nasal interface, forward of an effluent receptacle.

With particular reference to FIGS. 3-6, it can be seen that the housing also includes a lower housing wall 44 intended to support the fluid conduits forming the fluid passageway and a pump assembly 60 for directing the saline from the first bottle 12 to the second bottle 14. The first bottle is mounted to the controller 16 so that saline may be communicated to a saline supply conduit 46 and a supply bottle pressure relief conduit 48 (FIG. 6). The supply conduit passes through trigger 24 which may crimp the conduit or otherwise stop the flow of fluid through the conduit such as with a valve (not shown). The conduit 46 is normally closed by the crimp and will only communicate fluid from the bottle to a nasal interface upon the user activating the trigger 24. The supply conduit 46 directly communicates with first nozzle 40 so that the saline may be directed to the left nostril (as shown) of the user, pass through the nasal cavity and then be received in the second nozzle 42 for direct communication into the effluent bottle 14 through effluent conduit 50. Effluent bottle 14 is mounted to effluent bottle mount 52. The size and configuration of the conduits are not particularly limited other than to permit ready fluid flow. Sizes of 3/16 to 5/16 of an inch have proven operative. Minimizing the sharpness of conduit angle terms and appropriate volume metrics achieve the desired irrigating therapy. The effluent conduit 50 terminates in an effluent bottle mount 52 which provides air-tight and fluid-tight seals between the effluent bottle 14, conduit 50, and vacuum source conduit 54.

It is a feature of the embodiments that the vacuum pump assembly 60 is a source of relative vacuum within the device 10 to better facilitate the irrigating therapy by enhancing the flow with a suction force drawing the saline irrigant through the nasal cavity in addition to the gravity inducement of flow from the source bottle 12. It is believed that a vacuum source is an improved urging force relative to a user's health and therapeutic experience as opposed to pressure based pump devices which push the saline into the cavity and develop high pressure regions therein. Accordingly, vacuum pump 60 communicates the relative vacuum or negative pressure to the effluent bottle through the vacuum conduit 54 thereby facilitating drawing the saline through the nasal cavity and out the second nasal cushion 42. A pressure relief valve 64 is disposed such to limit the maximum amount of vacuum to not more than about 5.5 inches of mercury. Pressure relief valve 62 similarly permits air to replace the saline flowing out of supply bottle 12.

Electrical power is supplied to the pump 60 from a battery source 68 located in the handle base 26. The battery source may comprise replaceable or rechargeable batteries, or may alternatively comprise a corded power source for irrigating devices that may be continually employed in professional medical settings.

Figure 4:
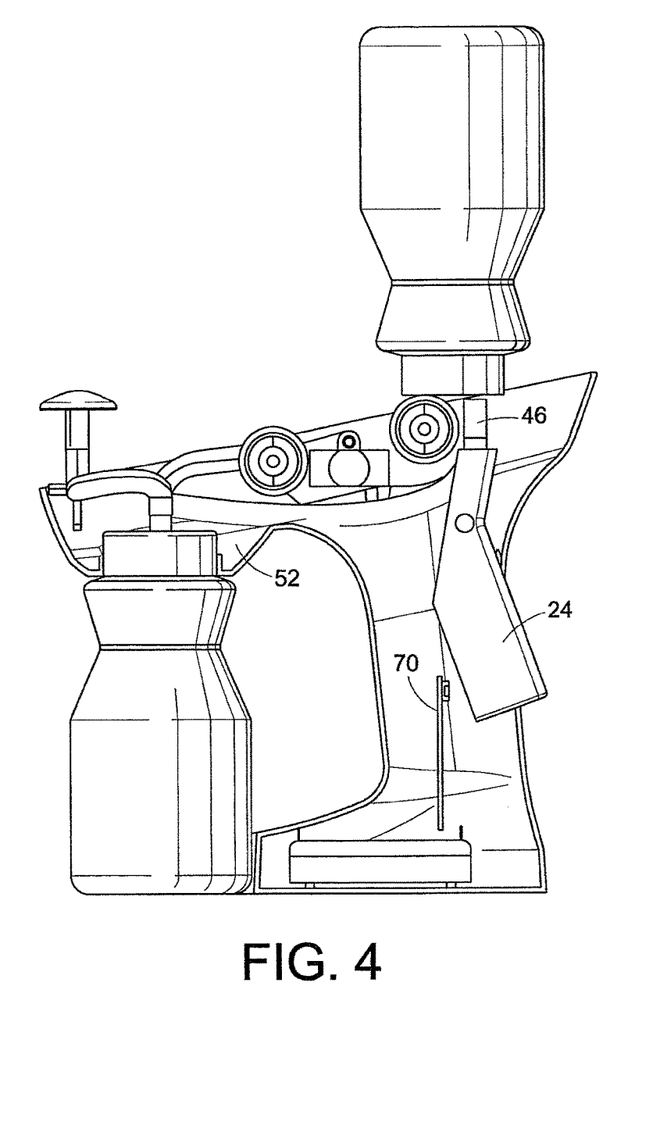
FIG. 4 is a partial cross-sectional view of the side elevation view of FIG. 2 wherein an outer sidewall is removed, again for showing internal elements.
Figure 5:
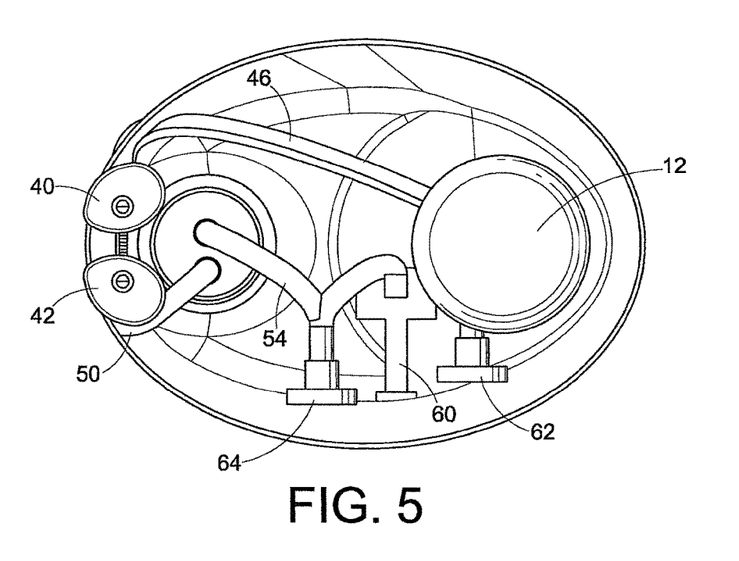
FIG. 5 is top plane view of the device corresponding to FIG. 3 wherein the top wall is also removed to similarly illustrate internal components.

With particular reference to FIG. 4, the trigger 24 operates to not only release the flow of saline through the supply conduit 46, but will also engage a switch 70 upon being pulled closed to supply electrical energy to the pump 60 from the battery supply 68.

Figure 2:
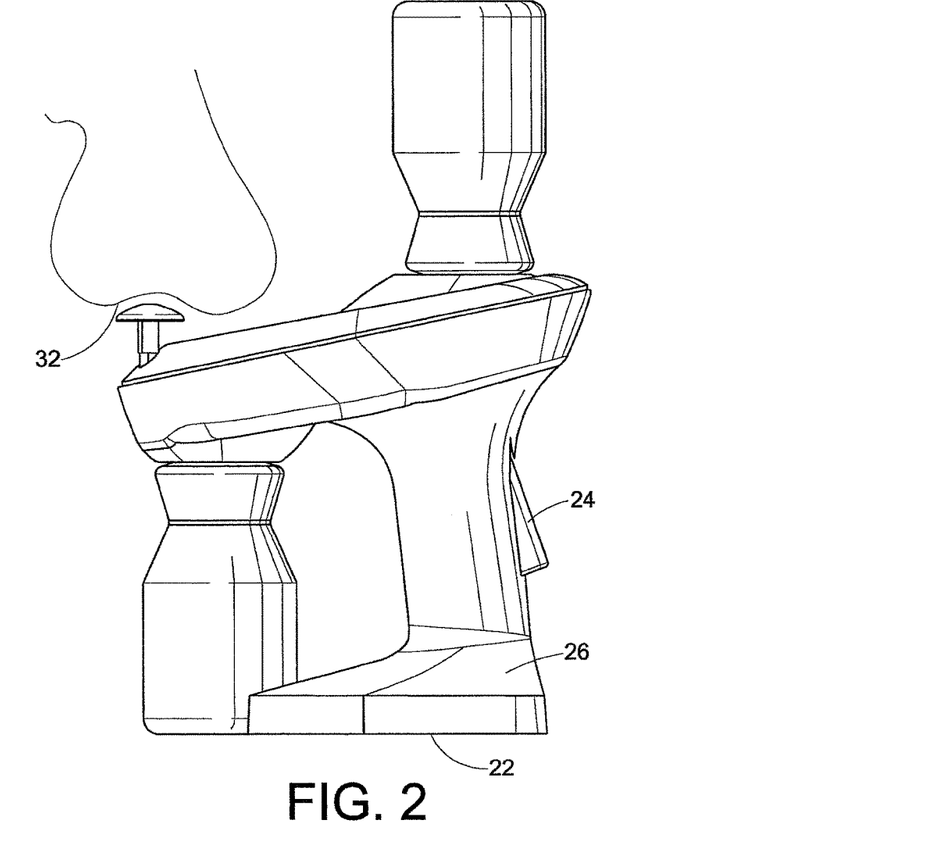
FIG. 2 is a side elevational view of the embodiment of FIG. 1.

In operation, the device 10 is disposed adjacent to the nostrils in a manner as shown in FIG. 2, by either being hand-held, or if being supported on a surface by moving the user's head to the intended engagement position. The user will pull the trigger 24 which will contemporaneously cause several consequences. It can be seen that the first bottle 12 is relatively disposed to the nasal cavity so that the saline is above the nasal cavity. The opening of the saline supply conduit 46 allows the saline fluid to flow to the first nozzle simply by gravity and similarly through the nasal cavity in the remaining fluid passageways, all by gravity. The use of the force of gravity alone is in fact one particular embodiment as will be discussed below. However, drawing the fluid through the nasal cavity by means of powered suction significantly enhances the washing, massaging, and rinsing elements that are central to effective nasal irrigation. In addition, the use of powered suction virtually eliminates the risk of applying painful and potentially harmful pressure to the Eustachian tube ostia in the nasal cavity. Since the flow is all downhill, a relatively small amount of vacuum is required to achieve the desired effect of drawing the saline around the posterior margin of the nasal septum and out the effluent naris. A miniature pump that generates vacuum in the range of from 3 to 5 PSI is sufficient for the purpose of adequately depressurizing the effluent bottle. However, an alternative embodiment (FIG. 12) may readily include a multi-speed pump source for varying the pressure based upon different trigger positions.

Figure 1:
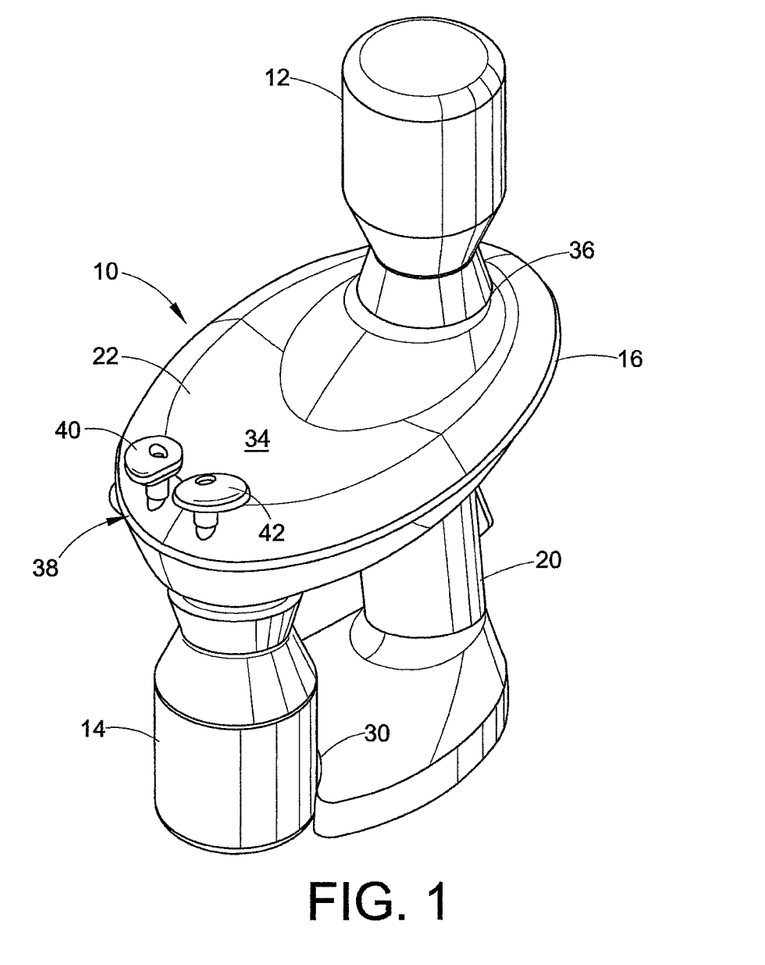
FIG. 1 is a perspective view of an embodiment of the subject nasal irrigation device.
Figure 7:
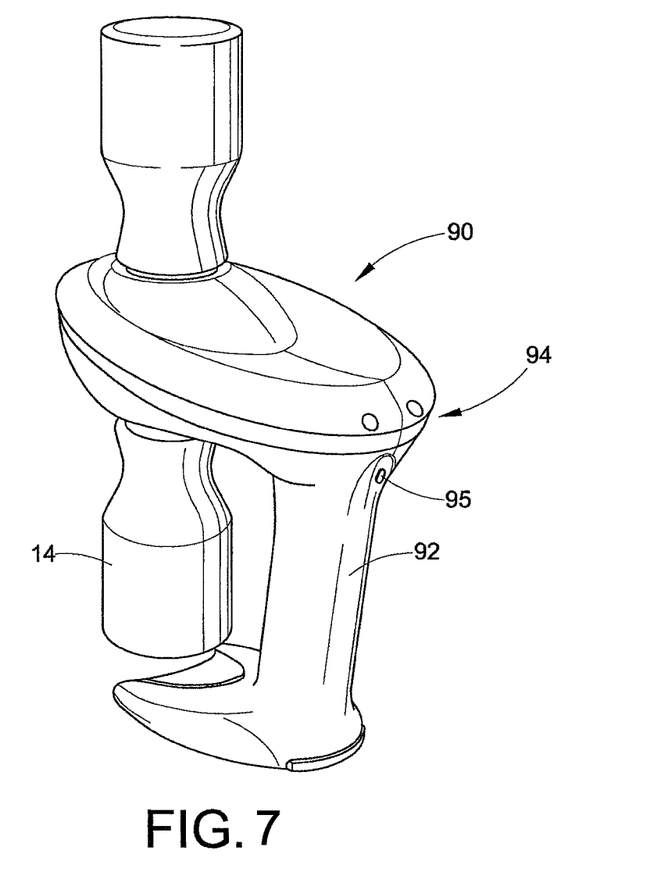

With particular attention to FIG. 7, an alternative embodiment 90 is shown in which the handle 92 is directly disposed below the nasal interface 94 and forward of the receptacle bottle 14, and includes a thumb switch 95 which operates to release the flow of saline and to supply electrical energy to the pump. Although the internal conduits comprising the fluid passageway within this embodiment 90 are slightly different in order to accommodate the alternative positioning of the bottle 14, the effective operation is the same and provides the advantage of not having to reach around the bottle 14 to grab the handle 20 as in the embodiment of FIG. 1.

The liquid supply should at least comprise a saline solution composed to avoid irritating the cavity. It has been found that a mix comprising various fragrances or tastes may enhance the experience, such as eucalyptus, chamomile, mint, or the like. It has also been found that buffering the solution with sodium bi-carbonate may enhance the experience. It has also been found that the use of hypertonic saline may enhance the experience. Alternative irrigants may also be used as well as medicine mixes such as an antibiotic, steroid or analgesics that are especially suited to nasal cavity delivery as rinses as opposed to absorbents.

The exemplary embodiments have been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A method for irrigating a nasal cavity including:
   sealing nares of a user to a hand-held device via first and second nozzles to form an associated closed fluid passageway in communication with a saline solution source and an effluent receptacle, wherein the passageway, source and receptacle are integrally assembled in the hand-held device, the source being disposed above the nasal cavity and the receptacle being disposed below the nasal cavity for defining a gravitationally induced flowpath through the fluid passageway;
   applying a relative vacuum to the effluent receptacle with a powered suction source also included in the hand-held device; and,
   releasing saline solution from the source into the passageway and the nasal cavity whereby a continuous flow of the saline solution through the nares and around a posterior margin of a nasal septum irrigates the nasal cavity, the flow being induced by a combination of gravity and the relative vacuum.

2. The method of claim 1 wherein the releasing is effected by user hand control of switch elements also included in the hand-held device.

3. The method of claim 1 further including collecting the saline solution expelled from the nasal cavity in the effluent receptacle.

4. The method of claim 3 further including removing the effluent receptacle from the device upon completing the irrigating.

5. The method of claim 1 including inserting a selectively removable saline cartridge in the device as the saline solution source.

6. The method of claim 1 wherein the effluent receptacle is disposed below the nares whereby the flow of the saline solution from the saline solution source is downhill.

7. A method for irrigating a nasal cavity including:
   sealing nares of a user to a hand-held device via first and second nozzles to form an associated closed fluid passageway in communication with a saline solution source and an effluent receptacle, wherein the passageway, source and receptacle are integrally assembled in the hand-held device and the source is disposed above the nasal cavity and the receptacle for defining a gravitationally induced flowpath through the fluid passageway; and,
   releasing saline solution from the source into the passageway and the nasal cavity whereby a flow of the saline solution through the nares and around a posterior margin of a nasal septum irrigates the nasal cavity, the flow being induced by gravity.

8. The method of claim 7 wherein the releasing is effected by user hand control of switch elements also included in the hand-held device.

9. The method of claim 7 further including collecting the saline solution expelled from the nasal cavity in the effluent receptacle.

10. The method of claim 9 further including removing the effluent receptacle from the device upon completing the irrigating.

11. The method of claim 7 including inserting a selectively removable saline cartridge in the device as the saline solution source.

12. The method of claim 7 wherein the saline solution source and effluent receptacle are vented and wherein the releasing includes gravity inducement of the saline solution into the passageway and receptacle.

* * * * *